United States Patent [19]

Goel et al.

[11] Patent Number: 4,652,655

[45] Date of Patent: Mar. 24, 1987

[54] BICYCLIC AMIDE ACETALS ARE PREPARED FROM ORGANIC NITRILES AND DIALKANOL AMINES AT BELOW ABOUT 140° C. AND PRODUCT IS ISOLATED BY SOLVENT EXTRACTION

[75] Inventors: Anil B. Goel, Worthington; Harvey J. Richards, Columbus, both of Ohio

[73] Assignee: Ashland Oil, Inc., Ashland, Ky.

[21] Appl. No.: 736,052

[22] Filed: May 20, 1985

[51] Int. Cl.$^4$ ............................................. C07D 498/04
[52] U.S. Cl. .................................... 548/217; 548/218; 548/219
[58] Field of Search ..................... 548/218, 219, 217

[56] References Cited

U.S. PATENT DOCUMENTS

| | | | |
|---|---|---|---|
| 2,448,890 | 9/1948 | Johnston | 548/218 |
| 4,501,679 | 2/1985 | Reierson et al. | 548/218 |

FOREIGN PATENT DOCUMENTS

| | | | |
|---|---|---|---|
| 2344607 | 3/1975 | Fed. Rep. of Germany | 548/218 |
| 2512980 | 12/1975 | Fed. Rep. of Germany | 548/218 |
| 2454740 | 5/1976 | Fed. Rep. of Germany | 548/218 |
| 3143251 | 5/1983 | Fed. Rep. of Germany | 548/218 |
| 3235933 | 3/1984 | Fed. Rep. of Germany | 548/218 |
| 1592467 | 6/1970 | France | 548/218 |

OTHER PUBLICATIONS

Chemische Werke Huels, Chem. Abst. 74-31744c.
Burzin, Chem. Abst. 81-25594.
Seeliger et al., Angnew Chem. Intenat. Edit. vol. 5, (10), pp. 875-888.
Feinauer, Synthesis (1971), pp. 16-26.

*Primary Examiner*—Donald G. Daus
*Assistant Examiner*—Cecilia Shen
*Attorney, Agent, or Firm*—John F. Jones

[57] ABSTRACT

An improved process for preparing bicyclic amide acetals from an organic nitrile and a dialkanol amine wherein the reaction temperature is maintained in the range of from room temperature to 140° C., and the bicyclic amide acetal product is removed from the reaction mixture by extraction into a hydrocarbon or organic nitrile solvent prior to its purification is described.

10 Claims, No Drawings

BICYCLIC AMIDE ACETALS ARE PREPARED FROM ORGANIC NITRILES AND DIALKANOL AMINES AT BELOW ABOUT 140° C. AND PRODUCT IS ISOLATED BY SOLVENT EXTRACTION

This invention relates to an improved process for the preparation of bicyclic amide acetals by the reaction of an organic nitrile with a dialkanol amine wherein the reaction temperature is maintained below about 140 degrees C. and the bicyclic amide acetal is removed from the reaction mixture by extraction in a hydrocarbon solvent.

The synthesis of bicyclic amide acetals by the reaction of a dialkanol amine, such as diethanol amine with alkyl nitriles has been reported to result in relatively low yields (30–40%) in *Angew Chem.* 85, (1973). A similar process is disclosed in German Patent Publication No. 2,344,607. Reaction temperatures used in this synthesis have been in the range of 120 to 180° C. Improvement in yields for such a process by the slow addition of the nitrile to the dialkanol amine and removal of the ammonia as it forms is described in copending U.S. patent application Ser. No. 641,242, filed 8/16/84. The preparation and reactions of bicyclic amide acetals are also described in *Synthesis*, (1971), pp. 16–26.

Although low yield synthesis of bicyclic amide acetals by the reaction of dialkanol amines and nitriles at 120 to 180 degrees C., usually in the presence of a catalyst such as an alkali metal, has been described, no reaction between the dialkanol amine and the bicyclic amide acetal at these temperatures has been disclosed. Because all of the bicyclic amide acetals boil at temperatures greater than 170 degrees C. under ambient pressure, and at these temperatures the dialkanol amine reacts with the bicyclic amide acetal, lower yields in the prior art process were inevitable. The use of solvent extraction to separate the bicyclic amide acetal from the reaction mixture to produce significantly higher yields has not previously been disclosed or suggested. The extraction solvent can be any inert solvent and can even include an excess of the starting nitrile itself.

The bicyclic amide acetals produced by the improved process of this invention include those having the Formula I

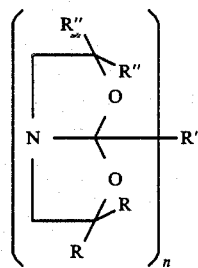

wherein n is 1 or 2, R and R'' independently represent hydrogen, an alkyl group having from 1 to 10 carbon atoms or an aryl group having from 6 to 12 carbon atoms, and when n is 1, R' represents an alkyl group having from 1 to 20 carbon atoms, an aryl group having from 6 to 12 carbon atoms, or an alkaryl group having from 7 to 20 carbon atoms, and when n is 2, R' represents an alkylene group having from 1 to 18 carbon atoms or an arylene group having from to 12 carbon atoms.

We have discovered that higher yields of purified bicyclic amide acetals can be obtained by separating the bicyclic amide acetal via solvent extraction prior any distillation of the bicyclic amide acetal. Thus, following the reaction of diethanol amine with an alkyl nitrile at a reaction between room temperature and 140° C. The reaction mixture in our process is subjected to extraction at about room temperature to isolate the bicyclic amide acetal product. The preferred solvents for the extraction of bicyclic amide acetal from the reaction mixture are hydrocarbons and hydrocarbon ethers having from 4 to 20 carbon atoms and most preferred are aliphatic hydrocarbons such as pentane, hexane, heptane, petroleum ether and aromatic hydrocarbons such as benzene and toluene. The starting nitriles themselves can also be used as extraction solvents in our invention. In the extraction the bicyclic amide acetals selectively go into the solvent layer and dialkanol amine and catalyst as well as high boiling byproducts remain in the remainder of the reaction mixture. The extracted bicyclic amide acetal, along with the nitrile and solvent can then be subjected to fractional distillation at any desired temperature without loss of yield. The use of an excess amount of the nitrile often obviates the necessity for any other solvent. The nitrile containing the bicyclic amide acetal separates and can be isolated readily from the remainder of the reaction mixture.

The organic nitriles useful in this process include aliphatic mononitriles having from 1 to 20 carbon atoms, aromatic mononitriles having from 7 to 15 carbon atoms and alkylaromatic mononitriles having from 8 to 20 carbon atoms and aliphatic dinitriles having from 3 to 22 carbon atoms, aromatic dinitriles having from 8 to 16 carbon atoms and alkaryl dinitriles having from 9 to 21 carbon atoms.

The dialkanol amines useful in the process of this invention include substituted and unsubstituted dialkanol amines having the general formula $HOC(R)_2CH_2NHCH_2C(R'')_2OH$ wherein R and R'' have the foregoing designations.

The process of this invention is further illustrated in the following representative examples.

EXAMPLE 1

Diethanol amine (0.26 g) and a bicyclic amide acetal of Formula I wherein n is 1, R and R'' are hydrogen and R' is benzyl (0.51) were mixed and heated in a closed mini reactor with constant stirring at 160° C. for 2½ hours. GLC analysis of the mixture showed that 47% of the diethanol amine and about 55% of the bicyclic amide acetal had reacted (were no longer present).

EXAMPLE 2

Diethanol amine (1.08 g) and a bicyclic amide acetal of Formula I where n is 1, R and R'' are hydrogen and R' is methyl (1.3 g) were mixed in a mini reactor and heated at 120° C. for three hours, followed by heating at 150° C. for two hours. GLC analysis of the mixture indicated that about 20% by weight of the starting diethanol amine and 25% of the bicyclic amide acetal had reacted.

EXAMPLE 3

Diethanol amine (1.05 g) and the bicyclic amide acetal of Formula I in which n is 1, R and R'' are hydrogen and R″ is methyl (1.25 g) were mixed and heated at 120° C. for three hours. GLC analysis showed the consumption of only about 2% by weight of each reactant.

EXAMPLE 4

The procedure of the prior art (German Patent Publication No. 1,344,607) was followed using 117.15 g of benzyl nitrile and 105.14 g of diethanol amine. The reaction was carried out at 140° C. for about 20 hours. The GLC analysis of the reaction mixture indicated the presence of about 65% by weight of the product of Formula I wherein n is 1, R and R″ are hydrogen and R′ is benzyl and about 10% by weight of benzyl nitrile and 4% of diethanol amine. The reaction mixture was subjected to fractional distillation under reduced pressure. Because of the high boiling nature of the product, the pot temperature had to be increased about 150° C. in order to distill the product at 110°–20° C./0.6–2 mm Hg pressure which afforded a 41% overall yield of the bicyclic amide acetal. The pot residue (95 g, 43%) was found to contain only traces of the product bicyclic amide acetal and was highly viscous indicating higher molecular weight byproducts. This shows that about 14% by weight of the bicyclic amide acetal product was lost during the isolation by distillation.

EXAMPLE 5

Diethanol amine (25.6 g) containing 2 mole percent of sodium and benzonitrile (25 g) were mixed and heated at 100° C. for 56 hours under nitrogen. The GLC analysis of the reaction mixture indicated the formation of about 38% by weight of bicyclic amide acetal of Formula I wherein n is 1, R is 1, R and R″ are hydrogen and R′ is phenyl. The reaction mixture was brought back to room temperature and the product and the unreacted benzonitrile were separated from diethanol amine.and the catalyst by extraction with three 40 ml portions of hexane and 20 ml of toluene. GLC analysis of the combined extracts showed them to contain mainly the nitrile and the bicyclic amide acetal product with only traces (less than 1%) of diethanol amine, whereas the residue was found to be mainly diethanol amine with traces (1 to 2%) of bicyclic amide acetal and nitrile. The solvent was removed from the extract and the residue was fractionally distilled giving a 35% yield of the bicyclic amide acetal (78°–79° C./0.02 mm Hg). This experiment demonstrates that essentially no loss of product occurs when separation of product by extraction is carried out prior to the distillation step which precludes possible reaction between the bicyclic amide acetal and diethanol amine.

EXAMPLE 6

The procedure of Example 5 was repeated using 52.7 g of diethanol amine with 2 mole percent of sodium and 90.7 g of undecyl nitrile. GLC analysis of the reaction mixture after 72 hours of reaction at 100° C. showed the formation of about 42% of the bicyclic amide acetal of Formula I in which n is 1, R and R″ are hydrogen and R′ is undecyl. The extraction with pentane (three 50 ml portions) and fractional distillation of the extract afforded about 52 g (greater than 38% yield) of the bicyclic amide acetal product.

EXAMPLE 7

A 40 g mixture containing approximately 50% by weight of diethanol amine, 45% of a bicyclic amide acetal of Formula I wherein n is 1, R and R″ are hydrogen and R″ is methyl and 5% of acetonitrile was extracted with three 80 ml portions of pentane at room temperature. The extracts were combined and analyzed and it was found that 95% of the total bicyclic amide acetal had been extracted. The GLC analysis of the residue not extracted showed the presence mainly of diethanol amine with about 5% of the bicyclic amide acetal.

EXAMPLE 8

A mixture of 20% by weight of the bicyclic amide acetal of Example 7 and 80% of diethanol amine. The bicyclic amide acetal was separated by extraction using acetonitrile as the solvent as in Example 7. GLC analysis of the residue left after extraction indicated the presence of 95% of diethanol amine and about 5% of the bicyclic amide acetal.

EMAMPLE 9

Acetonitrile (83.8 g, 2.04 mols) and diethanol-amine (88.2 g, 0.84 mol) containing 2 mole % of sodium (based on diethanol amine) as catalyst were reacted for 30 hours at 79° C. to produce the methyl bicyclic amide acetal of Formula I wherein n is 1, R and R″ are hydrogen and R′ is methyl in 75% yield. Separation of the bicyclic amide acetal product from the unreacted starting material and catalyst was accomplished with pentane solvent. The pentane extracted 93.5% of the bicyclic amide and no diethanol amine (GLC analysis). The mother liquor left after the extraction was found by GC to contain 100% of the unreacted diethanol amine and only 6.5% of the bicyclic amide acetal.

We claim:

1. In the process for preparing a bicyclic amide acetal from an organic nitrile and a dialkanol amine the improvement comprising conducting the reaction at a temperature in the range of from room temperature to 140° C. and then extracting the bicyclic amide acetal produce from the reaction mixture with a solvent selected from the group consisting of the organic nitrile, a hydrocarbon having from 4 to 20 carbon atoms and a hydrocarbon ether having from 4 to 20 carbon atoms.

2. The process of claim 1 wherein the bicyclic amide acetal is one conforming to the formula

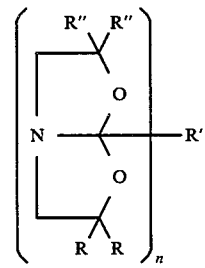

wherein R and R″ independently represent hydrogen, an alkyl group having from 1 to 10 carbon atoms or an aryl group having from 6 to 12 carbon atoms, and when n is 1, R′ represents an alkyl group having from 1 to 20 carbon atoms, an aryl group having from 6 to 14 carbon atoms, or an alkaryl group having from 7 to 20 carbon atoms and when n is 2, R′ represents an alkylene group having from 1 to 18 carbon atoms, an arylene group having from 6 to 14 carbon atoms or an alkarylene group having from 7 to 20 carbon atoms.

3. The process of claim 2 wherein the organic nitrile is one selected from the group consisting of an aliphatic mononitrile having from 1 to 20 carbon atoms, an aromatic mononitrile having from 7 to 15 carbon atoms, an alkaryl mononitrile having from 8 to 20 carbon atoms, an aliphatic dinitrile having from 3 to 22 carbon atoms, an aromatic dinitrile having from 8 to 16 carbon atoms and an alkaryl dinitrile having from 9 to 21 carbon atoms.

4. The process of claim 3 wherein the dialkanol amine is one which has the formula $HOC(R)_2CH_2NHCH_2C(R'')_2OH$ wherein R and R'' have the foregoing designations.

5. The process of claim 4 wherein the solvent is a member selected from the group consisting of the organic nitrile and a hydrocarbon containing from 2 to 20 carbon atoms.

6. The process of claim 4 wherein the organic nitrile is benzyl nitrile. The dialkanol amine is diethanol amine and the solvent is hexane and toluene.

7. The process of claim 4 wherein the organic nitrile is undecyl nitrile, the dialkanol amine is diethanol amine and the solvent is pentane.

8. The process of claim 4 wherein the organic nitrile is acetonitrile, the dialkanol amine is diethanol amine and the solvent pentane and acetonitrite.

9. The process of claim 4 wherein the organic nitrile is acetonitrile, the dialkanol amine is diethanol amine and the solvent is acetonitrile.

10. The process of claim 4 wherein the organic nitrile is acetonitrile, the dialkanol amine is diethanol amine and the solvent is pentane.

* * * * *